US006342470B1

(12) United States Patent
Aronson et al.

(10) Patent No.: US 6,342,470 B1
(45) Date of Patent: Jan. 29, 2002

(54) BAR COMPRISING SOAP, FATTY ACID, POLYALKYLENE GLYCOL AND PROTIC ACID SALTS IN CRITICAL RATIOS AND PROVIDING ENHANCED SKIN CARE BENEFITS

(75) Inventors: Michael Paul Aronson, West Nyack, NY (US); Charles Craig Nunn, Rutherford, NJ (US); Sergio Roberto Leopoldino, Sao Paulo (BR); John George Chambers, Wirral; Christine Gorman, Wirral Merseyside, both of (GB); Shana Azri-Meehan, River Vale, NJ (US)

(73) Assignee: Unilever Home & Personal Care USA, Greenwich, CT (US)

( * ) Notice: Subject to any disclaimer, the term of this patent is extended or adjusted under 35 U.S.C. 154(b) by 0 days.

(21) Appl. No.: 09/558,810

(22) Filed: Apr. 26, 2000

(51) Int. Cl.[7] .................................................. A61K 7/00

(52) U.S. Cl. ........................ 510/153; 510/152; 510/155; 510/141

(58) Field of Search ................................ 510/153, 152, 510/155, 141

(56) References Cited

U.S. PATENT DOCUMENTS 3,598,746 A 8/1971 Kaniecki et al.
3,723,325 A 3/1973 Parran, Jr.
4,954,282 A 9/1990 Rys et al.
4,976,953 A * 12/1990 Orr et al. ...................... 424/47
5,817,609 A 10/1998 He et al.
5,858,939 A * 1/1999 Tsaur ........................ 510/141

OTHER PUBLICATIONS

Applicant: Aronson et al. Serial No.: 09/558,821, Filed: Apr. 26, 2000 for: Method of Cleansing Skin and Imkproving Skin Care in Bar Comprising Soap, Fatty Acid and Polyalkylene Glycol.

Applicant: Aronson et al. Serial No.: 09/559,214 Filed: Apr. 26, 2000 for: Process of Making Soap Bar With Enhanced Skin Benefits.

* cited by examiner

*Primary Examiner*—Necholus Ogden

(57) ABSTRACT

The invention discloses bars comprising fatty acid soaps, free fatty acid, polyalkylene glycol and specific salts of protic acid (i.e., having pKa1 less than 6, preferably less than 5.5). Using specific equivalent molar ratios of free fatty acid to protic acid salt and specific wt. ratio of free fatty acid to PAG and salt of protic acid, applicants obtain bars having sensory feel of soap and which improve skin condition is measured in Controlled Application Wash Test.

22 Claims, 4 Drawing Sheets

Figure 1 Comparison Bar 1 and Bar 2 in induction of visual dryness.
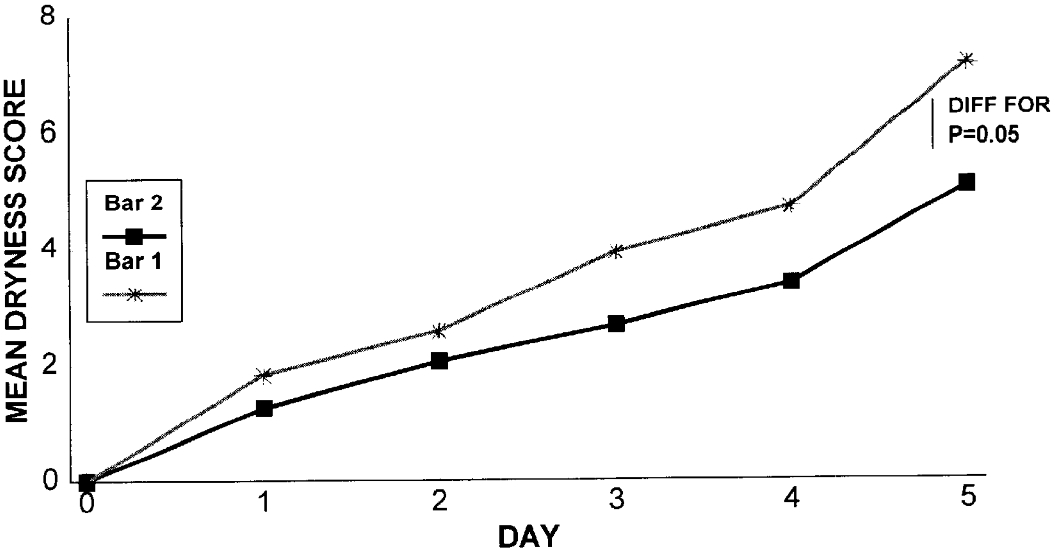

Figure 2. Comparison Bar 3 and Bar 4 in induction of visual dryness.
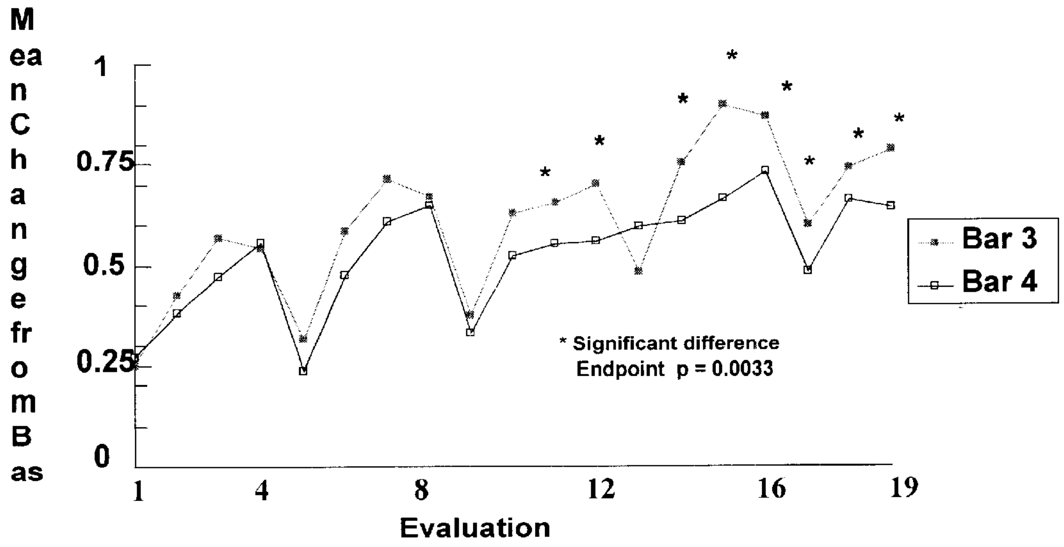

Figure 3. Comparison Bar 5 and Bar 6 in induction of visual dryness.
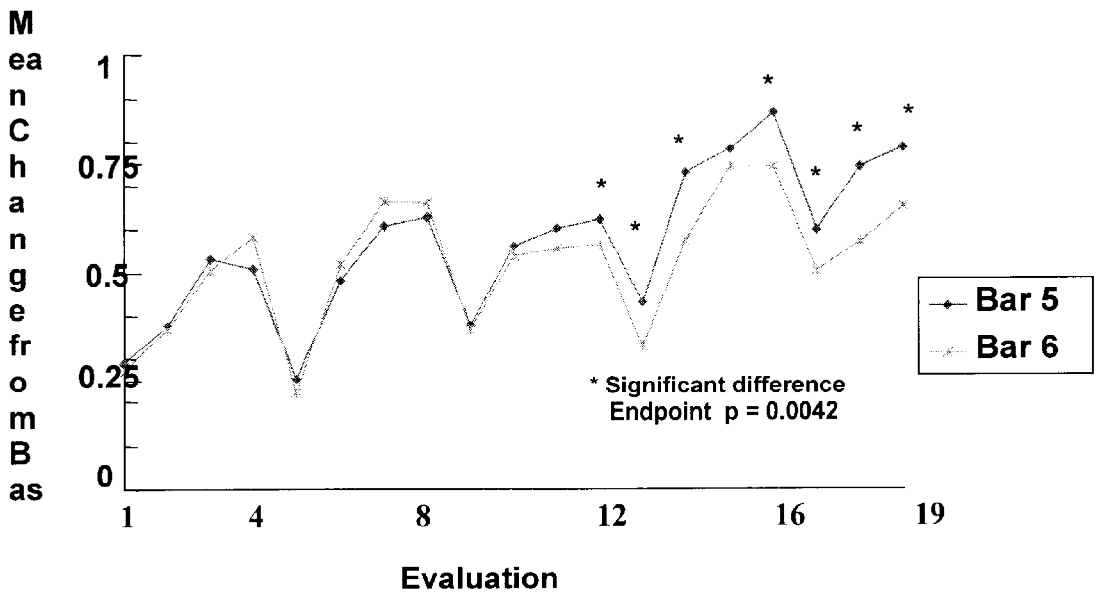

Figure 4. Critical weight ratios for Fatty acid to (PAG + Organic Protic Acid Salt)
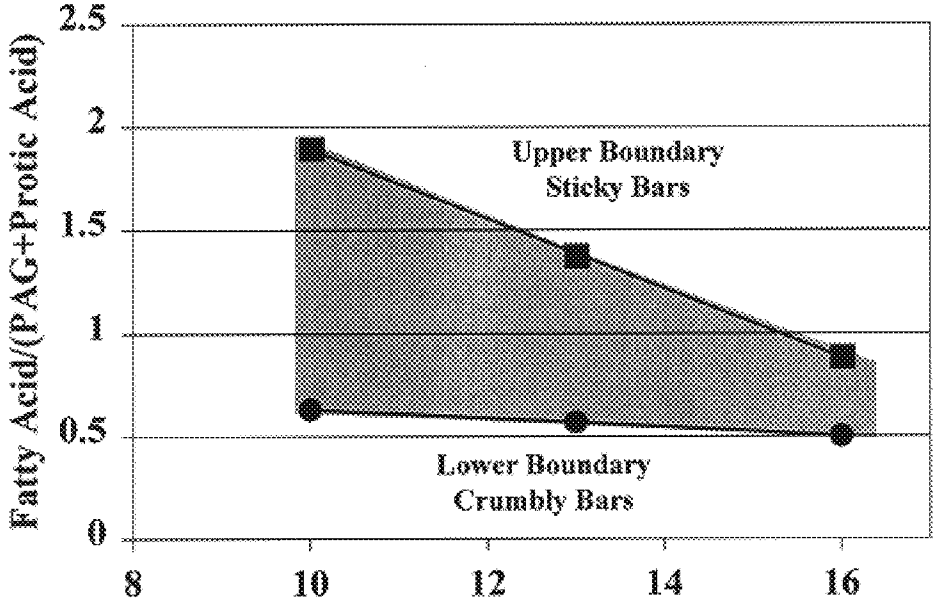

BAR COMPRISING SOAP, FATTY ACID, POLYALKYLENE GLYCOL AND PROTIC ACID SALTS IN CRITICAL RATIOS AND PROVIDING ENHANCED SKIN CARE BENEFITS

FIELD OF THE INVENTION

The invention relates to a personal washing bar that provides effective cleansing, and a refreshing experience while producing lower levels of visual dryness, retaining more moisture in the skin and maintaining a stronger protective barrier than ordinary soap. The composition comprises soap, polyalkalene glycol, fatty acid, and the salt of specific protic acids. The personal washing bar combines these benefits with excellent in-use sensory properties as well as good bar properties.

BACKGROUND

Consumers are increasingly interested in milder ways to cleanse their skin which results in less damage of the skin's natural protective barrier and also leads to the retention of more moisture in their skin. Indeed toilet bars based on synthetic surfactant such as the Dove® Beauty Bar have gained in popularity. Also, milder synthetic based liquids compositions are a growing segment of the market, especially among consumers in the more developed markets around the world.

However, the in-use properties of synthetic based bars and liquids (syndet bars and liquids) are quite different from soap. Synthetic based formulations tend to rinse slowly from the skin, often leave a feeling of a slippery residue remaining on the skin and are perceived not to last as long as soap. For many consumers in warm tropical climates, washing with syndet bars, combo bars and syndet liquids is not perceived to provide the level of cleansing and refreshing in-use sensory experience provided by soap and is a less preferred method of cleansing the skin even though washing with soap is harsher. Furthermore, because of the intrinsic cost of raw materials, packaging (for liquids), and the relatively higher use-up rates, mild syndet and combo bars and liquids makes these products out of reach of most consumers in emerging and developing markets even if they could learn to live with the very different cleansing experience.

There has been a great deal of research and development devoted to making soap bars milder. A recent review is provided by Murahata et al. (*Cleansing Bars for Face and Body: In Search of Mildness*, in Surfactants in Cosmetics, Ed M. Rieger and L. Rhein, 1997 Marcel Dekker, New York). The approaches include incorporation of relatively high levels of cationic polymers, mild synthetic surfactants, and the inclusion of a relatively high level of glycerol (>10%). All of these approaches have their limitations in terms of cost, manufacturing feasibility and impact on sensory properties and cost. One commercially successful approach is a so called "combo bar" of soap and a synthetic surfactant (e.g., acyl isethionate) as used for example in U.S. Pat. No. 4,954,282 to Resch et al. (relating to Lever 2000® type product). Even here, the sensory properties, use-up rates and cost do not match those of soap. Thus, there is a very real need for a method of cleansing the skin that is perceived to provide the refreshing cleansing experience and economy of soap while maintaining better skin care especially in the reduction of barrier damage and the increase in the level of moisture retention relative to common soap.

The present invention provides a method of cleansing the skin which is perceived as effective in removing oil and dirt, is preferred by consumers who like the sensory properties of soap, and provides improved skin care. In this context "improved skin care" is defined as causing less damage to the skin's naturally protective barrier, retention of more moisture in the skin, and/or reducing visible dryness than the method of cleansing the skin with an ordinary soap bar.

The invention further provides a bar which provides these cleaning and preferred sensory attributes while causing less damage to the skin's naturally protective barrier, inducing a lower level of visual dryness and while retaining more moisture in the skin than ordinary soap bars.

The invention further provides a bar which provides these desirable perceived cleaning, and preferred sensory properties, and delivery of improved skin barrier protection and moisturization, yet has a cost that is comparable with soap.

EP Patent No. 0,707,631 to Chambers et al. discloses a soap bar composition comprising:

(a) 44 to 86.5% by wt. fatty acid soap;

(b) 5 to 30% by wt. polyalkylene glycol;

(c) 2.5 to 20% by wt. $C_6$ to $C_{22}$ fatty acid; and (d) 6 to 20% water.

wherein ratio of polyalkylene glycol to $C_6$ to $C_{22}$ fatty acid is 1:3 to 3:1 and polyalkylene glycol has MW below 100,000 Dalton. There is no teaching of the specifically defined protic acid salts of the invention; of the ratios of these salts to free fatty acid; or of the sensory (soap-like clean) and skin care benefits (as measured by defined tests) provided when meeting the defined criteria of the invention.

Applicants have filed a continuation-in-part application to the equivalent of the U.S. Chambers application which claims 0.1 to 50% electrolyte and provides enhanced processing benefits. Again there is no teaching of the defined protic acid salts; of the ratios of these salts to free fatty acid or of enhanced skin care benefits.

Applicants have filed an application to Van Gunst et al. disclosing:

(a) 50 to 80% by wt. soap;

(b) 4 to 35% by wt. free fatty acid;

(c) 1 to 10% by wt. selected organic salts; and (d) about 10% water;

wherein the bar has no more than about 4% synthetic and is processed using standard extrusion equipment.

The reference fails to disclose the defined protic acid salts, the ratio of protic acid salts to free fatty acid or enhanced skincare benefits.

Similarly, U.S. Pat. No. 3,598,746 to Kaniecki discloses soap free fatty acid and polyalkylene glycol, but fails to recognize defined protic acid salts, ratio of salts to free fatty acid or sensory properties and skin care benefits as measured in the subject invention.

BRIEF DESCRIPTION OF THE INVENTION

The subject invention provides bar comprising fatty acid soaps, free fatty acids, polyalkylene glycol and specifically defined protic acid salts. Using these protic acid salts and defined ratios of the protic acid salts to free fatty acids, applicants have unexpectedly been able to obtain enhanced skin care properties as measured by defined tests, while achieving good desirable bar properties (e.g., hardness, low grit) and desirable sensory properties (e.g., clean rinsing).

More specifically, the invention comprises:

(a) 25 to 85% by weight fatty acid soap;

(b) polyalkylene glycol having MW of 400 to 25,000, preferably 400 to 10,000;

(c) 1 to 35% by weight $C_8$–$C_{22}$, preferably $C_{10}$–$C_{20}$, more preferably $C_{10}$–$C_{18}$ free fatty acid (saturated and unsaturated, preferably at least saturated); and (d) 0.1 to 5% by wt., preferably 0.5 to 3% by wt. of a salt of a protic acid having a pKa1 of less than 6, preferably less than 5.5;

wherein the amount of polyalkylene glycol present in the bar must be sufficient to improve skin condition in Controlled Application Wash Tests either by reducing the barrier damage as measured by transepidermal water loss, increasing skin hydration as measured by skin conductivity/capacitance, and/or by reducing visual dryness as measured by objective grading.

In addition, the molar equivalents ratio of free fatty acid to protic acid salt is preferably between 0.5:1 to 3:1, most preferably between 0.75:1 to 3:1 and the weight ratio of free fatty acid to the sum of weights of PAG plus protic acid salt, i.e., (wt. % FA)/(wt. % PAG+wt. % protic acid salt) , should be between 1:2 to 2:1.

The molar equivalent ratio is defined by the following equation:

Grams Free Fatty Acid/Molecular Weight Free Fatty Acid (Grams protic acid/Molecular Weight Protic acid)×(Number Equivalents per Mole Protic Acid)

The term equivalents is used in the ordinary chemical sense for protic acids and is equal to the number of moles of hydronium ions required to form the fully protonated conjugate acid of the protic acid salt.

BRIEF DESCRIPTION OF THE DRAWINGS

FIG. 1 is graph showing reduction in the induction of visual dryness using Bar 2 of invention versus Comparison Bar which does not contain polyalkylene glycol.

FIG. 2 shows reduction in induction of visual dryness for Bar 4 of invention versus Comparative Bar 3.

FIG. 3 shows reduction in induction of visual dryness for Bar 6 of invention versus Bar 5.

FIG. 4 shows critical ratios of free fatty acid to polyalkylene glycol plus protic acid salt with regard to processability of bars.

DETAILED DESCRIPTION OF THE INVENTION

The present invention relates to bars comprising fatty acid soap, free fatty acid polyalkylene glycol, and specific salts of protic acid. By using specifically defined salts of protic acids (i.e., defined pKa1) molar equivalent ratios of protic acid salt to free fatty acid and weight ratios of free fatty acid to polyalkylene glycol plus salt of protic acid, applicants have unexpectedly found it is possible to obtain bars with enhanced skin care properties as measured by defined tests. These bars also have excellent sensory properties, particularly relevant to oily skinned people who prefer the cleansing feeling of soap. Further these bars have good bar properties, e.g., adequate hardness and low grittiness.

Each of these criticalities is defined in greater detail below.

Fatty Acid Soaps

Bars of the invention comprise about 25% to 85%, preferably about 50% to 75% fatty acid soap.

The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for purposes of this invention. In general, sodium soaps are used in the compositions of this invention, but from about 1% to about 25% of the soap may be potassium or magnesium soaps. The soaps useful herein are the well known alkali metal salts of natural of synthetic aliphatic (alkanoic or alkenoic) acids having about 8 to 22 carbon atoms, preferably about 8 to about 18 carbon atoms. They may be described as alkali metal carboxylates of acrylic hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 30% to about 40% coconut oil and about 60% to about 70% tallow. Mixtures may also contain higher amounts of tallow, for example, 15% to 20% coconut and 80 to 85% tallow.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

Fatty acid soap should comprise 25–85% by wt., preferably 50% to 75% by wt. of final composition.

Fatty Acid

A second required component of the invention is free fatty acid. This "superfat" traditionally would not be added in large amounts to bar compositions to replace synthetic surfactant because it would cause bars to be tacky, suffer discoloration or have poorer lather. By tacky is meant that the bar product is sticky and leaves a residue on the hands when the dry bar or extruded log is touched. Sticky/tacky bars stick undesirably to extrusion equipment including chamber walls and press. Generally such bars will have reduced throughput. According to the subject invention, however, the fatty acid can be added in amounts ranging from 1 to 35%, preferably 2% to 30%, and most preferably 2 to 14% by wt. of the bar composition.

By free fatty acid is meant C8–C22, preferably C12–C18, more preferably C16–C18, preferably saturated, straight-chain fatty acids. However, some unsaturated fatty acids can be employed.

Of course the free fatty acids can be mixtures of shorter (e.g., C10–C14) and longer (e.g., C16–C18) chain fatty acids although it is preferred that longer chain fatty acids predominate over the shorter chain fatty acids.

Polyalkylene Glycol

A third required component of the invention is use of polyalkylene glycol.

Polyalkylene glycols include polyethylene glycols, polypropylene, block and random copolymers of ethylene oxide and propylene oxide, and their mixtures.

Another useful class of polyalkylene glycols are polyethylene glycol, especially those with MW greater or equal to 1000 that are hydrophobically modified by substitution on one or more of the terminal hydroxyl groups with long chain alkyl or acyl groups.

Especially preferred polyalkylene glycols are polyethylene glycols of MW from about 300 to 25,000, preferably 300 to 10,000 and more preferably 400 to 8000.

The amount of polyalkylene glycol present in the bar must be sufficient to improve skin condition in Controlled Application Wash Tests either by reducing the barrier damage as measured by transepidermal water loss, increasing skin hydration as measured by skin conductivity/capacitance, and/or by reducing visual dryness. In practice, this requires a level of PAG in range of about 0.5 to 30%, preferably 1.5 to 25%, more preferably 2 to about 15% by wt.

Salt of Protic Acid

A fourth required component of the invention is a salt of a protic acid. A protic acid commonly is any acid that readily yields protons, i.e., a Bronstead Acid. More specifically, the protic acid salt should have pKa1 (referring to the first proton to be donated) of less than 6, preferably less than 5.5.

Among the salts of such protic acids are selected inorganic and organic acids. The specific inorganic protic acids salts include the magnesium, potassium and especially sodium salts of hydrochloric acid, sulfuric acid, phosphoric acid, carbonic acid, and pyrophosphoric acid. The selected organic protic acid salts include the magnesium, potassium and especially sodium salts of adipic acid, citric acid, glycolic acid, acetic acid, formic acid, fumaric acid, lactic acid, malic acid, maleic acid, succinic acid, tartaric acid and polyacrylic acid.

Especially preferred salt of an inorganic acids are sodium chloride, sodium sulfate and sodium phosphate. Especially preferred salts of organic protic acid are sodium citrate, sodium lactate, and sodium adipate.

The amount of polyalkylene glycol present in the bar must be sufficient to improve skin condition in Controlled Application Wash Tests either by reducing the barrier damage as measured by transepidermal water loss, increasing skin hydration as measured by skin conductivity/capacitance, and/or by reducing visual dryness.

In addition, preferably the molar equivalents ratio of free fatty acid to protic acid salt is preferably between 0.5:1 to 3:1, most preferably between 0.75:1 to 3:1 and the weight ratio of free fatty acid to the sum of weights of PAG plus protic acid salt, i.e., (wt. % FA)/(wt. % PAG+wt. % protic acid salt), should be between 1:2 to 2:1.

The molar equivalent ratio is defined by the following equation:

Grams Free Fatty Acid/Molecular Weight Free Fatty Acid
(Grams protic acid/Molecular Weight Protic acid)×
(Number Equivalents per Mole Protic Acid)

The term equivalents is used in the ordinary chemical sense for protic acids and is equal to the number of moles of hydronium ions required to form the conjugate acid of the protic acid salt.

Optional

Although bars of the invention are primarily fatty acid soap bars, some small percentage (e.g.,10% and below, preferably 0.01–5%, of auxiliary surfactant may be synthetic surfactant. This includes anionic surfactants, nonionic surfactants, amphoteric/zwitterionic surfactants, cationic surfactants, etc. such as are well known to the person skilled in the art. Among the many surfactants which may be used are those described in U.S. Pat. No. 3,723,325 to Parran Jr. et al. "Surface Active Agents and Detergents (Vol. I & II) by Schwartz, Perry and Berch, both of which are incorporated by reference into the subject application.

Examples of suitable anionic surfactants useful as auxiliary surfactants include: alkane and alkene sulfonates, alkyl sulfates, acyl isethionates, such as sodium cocoyl isethionate, alkyl glycerol ether sulfonates, fatty amidoethanolamide sulfosuccinates, alkyl citrates, and acyl taurates, alkyl sarcosinates, and alkyl amino carboxylates. Preferred alkyl or alkenyl groups have C12–18 chain lengths.

Examples of suitable nonionic surfactants include: ethoxylates (6–25 moles ethylene oxide) of long chain (12–22 carbon atoms) alcohol (ether ethoxylates) and fatty acids (ester ethoxylates); alkyl polyhydroxy amides such as alkyl glucamides; and alkyl polyglycosides.

Examples of suitable amphoteric surfactants include simple alkyl betaines, amido betaines, especially alkyl amidopropyl betaines, sulfo betaines, and alkyl amphoacetates.

Additives such as dyes, perfumes, soda ash, sodium chloride or other electrolyte, brighteners, etc. are normally used in an amount 0 to 3%, preferably 0.01 to 2% of the composition. Some examples are set forth below.

Perfumes; sequestering agents, such as tetrasodium ethylene diaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The bar may also include compatibilizing agents such as propylene glycol, glycerol and sorbitol.

In addition, the bar compositions of the invention may include 0 to 25% by wt., preferably 1 to 25% by wt., more preferably 5 to 20% by wt. skin protection and benefit agents and/or performance enhancers optional ingredients as follows:

Further, the bar composition of the invention may include 0 to 25% by weight of crystalline or amorphous aluminium hydroxide. The said aluminium hydroxide can be generated in-situ by reacting fatty acids and/or non-fatty mono- or polycarboxylic acids with sodium aluminate, or can be prepared separately by reacting fatty acids and/or non-fatty mono- or polycarboxylic acids with sodium aluminate and adding the reaction product to the soap.

Such optional additives may further include starches and various water soluble polymers chemically modified with hydrophobic moiety (e.g., EO-PO block copolymer); modified starches and maltodextran.

Other optional additives may include one or more of structurants such as soluble alkaline silicate, kaolin, talc, calcium carbonate, inorganic electrolytes such as tetra sodium pyrophosphate, organic salts such as sodium citrate, sodium acetate, and modified starches.

Another class of optional ingredients are antimicrobials such as but not limited to the following:

2-hydroxy-4,2',4'-trichlorodiphenylether (DP300);

2,6-dimethyl-4-hydroxychlorobenzene (PCMX);

3,4,4'-trichlorocarbanilide (TCC);

3-trifluoromethyl-4,4'-dichlorocarbanilide (TFC);

2,2'-dihydroxy-3,3',5,5',6,6'-hexachlorodiphenylmethane;

2,2'-dihydroxy-3,3',5,5'-tetrachlorodiphenylmethane;

2,2'-dihydroxy-3,3',dibromo-5,5'-dichlorodiphenylmethane;

2-hydroxy-4,4'-dichlorodiphenylether;

2-hydroxy-3,5',4-tribromodiphenylether; and 1-hydroxyl-4-methyl-6-(2,4,4-trimethylpentyl)-2(1H)-pyridinone (Octopirox).

Other suitable antimicrobials include:

Benzalkonium chloride;

Benzethonium chloride;

Carbolic acid;

Cloflucarbon (Irgasan CF3:4,4'-dichloro-3-(trifluoromethyl)carbanilide);

Chlorhexidine (CHX: 1,6-di(4'-chlorophenyl-diguanido) hexane);

Cresylic acid;

Hexetidine (5-amino-1,3-bid(2-ethylhexyl)-5-methylhexahydropyrimidine);

Iodophors;

Methylbenzethonium chloride;

Povidone-iodine;

Tetramethylthiuram disulfide (TMTD: Thiram);

Tribrominated salicylanilide.

Additional antimicrobials include tea tree oil, zinc salts, any of the above noted antimicrobials and mixtures thereof.

The compositions may also comprise preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate. Cationic polymers as conditioners which may be used include Quatrisoft LM-200 Polyquaternium-24, Merquat Plus 3330—Polyquaternium 39; and Jaguar® type conditioners.

Polyethylene glycols as conditioners which may be used (in addition to required polyalkylene glycol of invention) include:

| | | |
|---|---|---|
| Polyox | WSR-205 | PEG 14M, |
| Polyox | WSR-N-60K | PEG 45M, or |
| Polyox | WSR-N-750 | PEG 7M. |

Another ingredient which may be included are exfoliant particles such as polyoxyethylene beads, walnut shells apricot seeds and silica.

Benefit Agent

The benefit agent optionals of the subject invention may be a single benefit agent component, or it may be a benefit agent compound added via a carrier into the process stream. Further the benefit agent may be a mixture of two or more compounds, one or all of which may have a beneficial aspect. In addition, the benefit agent itself may act as a carrier for other components one may wish to add to the bar composition.

The benefit agents can be emollients, moisturizers, anti-aging agents, skin-toning agents, skin lightening agents, sun screens etc.

The preferred list of benefit agents include:

(a) silicone oils, gums and modifications thereof such as linear and cyclic polydimethylsiloxanes; amino, alkyl alkylaryl and aryl silicone oils;

(b) fats and oils including natural fats and oils such as jojoba, soybean, sunflower seed oil, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, petrolatum, vaseline, microcrystalline wax, ceresin, squalene, pristan, paraffin wax and mineral oil;

(f) higher fatty acids such as behenic, oleic, linoleic, linolenic, lanolic, isostearic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX), octocrylene(2-ethylhexyl 2-cyano-3,3-diphenylacrylate), octyl salicylate (2 ethylhexyl salicylate), benzophenone-3 (2-hydroxy-4-methoxy benzophenone), and avobenzone (4-tert-butyl-4'-methoxydibenzoylmethane) (these are merely illustrative);

(m) phospholipids; and (n) mixtures of any of the foregoing components.

A particularly preferred benefit agent is silicone, preferably silicones having viscosity greater than about 50,000 centipoise. One example is polydimethylsiloxane having viscosity of about 60,000 centistokes.

Another preferred benefit agent is benzyl laurate.

When the benefit agent is an oil, especially a low viscosity oil, it may be advantageous to pre-thicken it to enhance its delivery. In such cases, hydrophobic polymers of the type described in U.S. Pat. No. 5,817,609 to He et al may be employed, which is incorporated by reference into the subject application.

The benefit agent generally comprises about 0–25% by wt. of the composition, preferably 5–20%, and most preferably between 2 and 10%.

Bar Manufacture

The bars described in this application can be prepared using manufacturing techniques described in the literature and known in the art for the manufacture of toilet soap bars. Examples of the types of manufacturing processes available are given in the book *Soap Technology* for the 1990's (Edited by Luis Spitz, American Oil Chemist Society Champaign, and Illinois. 1990). These broadly include: melt forming, extrusion/stamping, and extrusion, tempering, and cutting. A preferred process is extrusion and stamping because of its capability to economically produce high quality bars suitable as toilet soaps.

The key process step is to create a uniform mixture of fatty acid soap, free fatty acid, PAG, and protic acid salt under mixing conditions at a temperature of 25 and 45 C., preferably at a temperature between 30 and 40 C. and most preferably between 30 and 35 C. This temperature is require to gain the maximum benefits of this combination in providing bars having superior skin care properties, user properties, and manufacturability. A part or all of the free fatty acid and protic acid salt can be added separately or part or all of these components can be generated in-situ via the addition of the protic acid to the soap mixture under the process conditions described. Either route can provide suitable bars.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

METHODOLOGY

1. Controlled Application Wash Tests

Various clinical test methods have been developed to quantify the effects of cleansers on the skin, particularly to examine their relative potential to induce irritation, skin barrier damage, and dryness. These tests generally fall into two categories: i) those which employ prolonged contact of a test solution with the skin, and ii) those that utilize a controlled washing protocols which involve frequent cleanser application to simulate exaggerated use within a short time period (typically one week). Examples of the former are the occluded patch test, and the soap chamber test. Controlled washing protocols include the Flex-Wash, and the Arm-Wash (using two or four test sites). Another example is the Forearm Controlled Application Test (FCAT) which more closely mimics actual consumer washing regimens, as discussed by Nicoll et al (*The relative sensitivity of two arm-wash test methods for evaluating the mildness of personal washing products*, J Soc. Cosmet. Chem., 46, 129 (1995)). The latter protocols described above simulate in-home use conditions, can differentiate between formulations and may be more predictive of the skin effects that may develop. They are also considered to be more realistic than protocols that traditionally induced high levels of erythema and dryness (M. F Lukacovic, F. E. Dunlap, S. E. Michaels, M. O. Visscher, and D. D. Watson, *Forearm Wash Test to evaluate the mildness of cleansing products*, J. Soc. Cosmet. Chem., 39, 355–366 (1988)).

The methodology employed to evaluate the effects of the present invention on skin condition employs the Controlled Washing Tests described below. These tests utilize a combination of subjective evaluations (visual skin condition assessment by expert graders) as well as objective measures, i.e. instrumental biophysical measurements to quantitate cleanser induced changes to the skin's barrier function and skin's ability to retain moisture.

Standard Arm Wash Test

This test has been described in detail and validated by Sharko et al (*Arm wash evaluation with instrumental evaluation—A sensitive technique for differentiating the irritation potential of personal washing products*, J. Derm. Clin. Eval. Soc. 2, 19 (1991)). A description of the protocol follows:

Subjects report to the testing facility for the conditioning phase of the study, which consists of using an assigned marketed personal washing cleanser for general use at home, up to four days prior to start of the product application phase. On Day 1 of the product application phase, a visual assessment is made to determine subject qualification. Subjects must have dryness scores $\leqq 1.0$ and erythema scores $\leqq 0.5$, and be free of cuts and abrasions on or near the test sites to be included in the product application phase. Subjects who qualify to enter the product application phase will be instructed to discontinue the use of the conditioning product and any other skin care products on their inner forearms, with the exception of the skin cleansing test formulations that are applied during the testing visits. During the five (5) day product application phase of the study, visual assessments for dryness and erythema are conducted prior to each wash session. Wash sessions are conducted 4 times daily, approximately 1.5 hours apart for the first four (4) days. On the last day, there are two (2) wash sessions followed by a final visual evaluation three hours after the final wash. Each application consists of a one or two-minute wash. In the examples shown below, a total of 18 washes and 19 evaluations performed in this protocol. Instrument measurements were taken at baseline and at the last evaluation.

Washing Procedure:

1) Timer is set to designated wash time (up to two minutes)
2) The left test site (volar forearm) is moistened with warm water (90°–100° F.).
3) Product is dispensed, lather is generated and the timer is started.
4) The site is washed in a back and forth motion, one stroke per second (a stroke is from the inner elbow to the wrist and back to the inner elbow) for the designated time.
5) The fingertips are re-wet at the midpoint of the wash i.e. at 30 sec for a one minute wash.

6) The site is rinsed with warm running water and patted dry.

7) The above procedure (1–6) is repeated for the right test site.

For Bar Products: the bar is picked up, gloved hands and bar are moistened and the bar is rotated ten times to generate the lather. A metronome may be used to guide the subjects washing rate (60 beats/minute).

Evaluation Methods

Baseline visual assessments are made prior to the start of the product application phase, and immediately before each wash session to evaluate dryness and erythema thereafter. Washing of a test site will be discontinued if a clinical dryness or erythema score of >3.0 is reached, or at the subject's request. If only one arm is discontinued, the remaining arm will continue to be washed according to schedule. The same evaluator under conditions that are consistent throughout the study will conduct all of the visual evaluations. The 0–4 grading scale shown in Table 1 is used to assess the test sites for dryness and erythema. To maintain the evaluator's blindness to product assignment, the visual assessments will be conducted in a separate area away from the product application area.

TABLE 1

| Grade | Erythema | Dryness |
|---|---|---|
| 0 | None | None |
| 0.5 | Perceptible erythema | Perceptible dryness, whiteness in lines of the skin (fine white lines) |
| 1.0 | Mild, slight erythema | Slight flaking/uplifting of flakes (patchy and/or powdered appearance. |
| 1.5 | Slight to moderate erythema | Slight to moderate flaking/uplifting flakes (uniform). |
| 2.0 | Moderate, confluent erythema | Moderate flaking/uplifting flakes, (uniform) and/or slight scaling. |
| 2.5 | Moderate to marked erythema | Moderate to severe flaking/uplifting flakes and/or moderate scaling. |
| 3.0 | Marked, prominent erythema | Severe flaking/scaling, uplifting of scales and/or slight fissuring |
| 3.5 | Deep erythema | Severe scaling/uplifting scales and/or moderate fissuring |
| 4.0 | Fiery, deep erythema | Severe scaling/uplifting scales; with severe fissuring/cracking |

Transepidermal Water Loss (TEWL) measurements for barrier integrity are made on each test site using a Servomed Evaporimeter EP1 and/or EP2 at the beginning (baseline value), and at the end of the product application phase or at the time of discontinuation (final value). Two consecutive fifteen-second readings per test site are taken for each TEWL evaluation, following a thirty-second equilibration period.

Skin conductance is measured using a SKICON-200 instrument, with an MT-8C probe, and/or Capacitance is measured using a Corneometer, at the beginning (baseline value), and at the end of the product application phase or at the time of discontinuation (final value). These methods provide objective measures of stratum corneum hydration. Three consecutive readings per test site will be taken and averaged.

Data Analysis

If product application has been discontinued on a test site due to a dryness or erythema score of ≧3.0 all data (clinical grades) at that evaluation for that subject are carried forward for the remaining time points. Data for the discontinued sites are used such that the last acceptable reading (i.e. the last fair comparison) is used as the endpoint in the analysis. Actual data for the discontinued sites is recorded, but not included in the statistical analysis.

The dryness and erythema scales are treated as ordered categorizations; hence, nonparametric statistical methods are used. At each evaluation point, the differences in clinical grades (evaluation score subtracting the baseline score) within each product is evaluated using the Wilcoxon Signed-Rank test, Pratt-Lehmann version (Lehmann, E. L. *Non-parametrics: Statistical Methods Based on Ranks*. San Francisco, Calif.: Holden Day, 1975, pg.130). Statistical significance will be determined at the 90% confidence level ($p<0.10$). This will indicate if the treatment results are statistically significant from their baseline score.

Means, median scores, and mean ranks across all subjects for each treatment at each evaluation point are calculated and recorded. At each evaluation point, the differences in clinical grades (evaluation-baseline) for each test product is evaluated using the Wilcoxon Signed-Rank test, Pratt-Lehmann version. This indicates if the products are statistically significantly different from each other (90% confidence level ($p<0.10$).

For the instrumental data, the same comparisons are made using parametric statistical methods. The TEWL and conductance measurements are averaged separately for each subject, site, and session. For all treatments, treatment differences are statistically compared using a paired t-test at each evaluation point. Statistical significance will be determined at the 90% confidence level ($p<0.10$).

The data will also be assessed to determine whether one treatment impacts skin condition to a greater degree relative to the other test cell through the number of discontinuations. For each attribute, a survival analysis will examine treatment performance over wash sessions. The analysis will incorporate the number of wash sessions that a subject's treatment site is actually washed in the study. If the treatment site is discontinued, then the site's survival time is determined at that evaluation. An overlay plot of the estimated survival function for each treatment group will be examined. The Log-Rank test statistic will be computed to test for homogeneity of treatment groups. This test will tell if the survival functions are the same for each of the treatment groups. Also, the number of wash sessions survived by a treatment site during the study (prior to the possible discontinuation of that side) will be compared between treatments via a paired t-test, using the test subject as a block.

If dryness and erythema rank scores are also assigned at each evaluation, the treatments will be compared with respect to the rank scores by application of the Friedman's test on the ranks, with subject acting as a block [ref. Hollander, Myles and Douglas A. Wolfe. *Nonparametric Statistical Methods*. New York, N.Y. John Wiley & Sons, 1973, pp. 139–146].

At each evaluation, if Friedman's test examining treatment effects is significant at a p-value of 0.05 or other preselected level, then multiple comparison tests comparing each pair of treatments will be performed. For comparison of all possible pairs of treatments, the procedure documented in Hollander and Wolfe pp. 151–155 will be used. This test is based on the Friedman rank sums. For comparison of treatments vs. a control, the procedure documented in Hollander and Wolfe pp. 155–158 will be used.

4-Site Arm Wash Test

The 4-Site Arm Wash is very similar to the Standard Arm Wash protocol described above with the exception that each forearm is divided into two sites and the sites are typically washed for a shorter duration. In this protocol, four separate compositions can be examined and compared. The visual grading, instrumental assessments, and data analysis are the same as that described above and essentially by Sharko et al.

Washing Procedure:

1. The washing of both forearms can be conducted simultaneously.
2. Timer is set to designated wash time (up to two minutes)
3. The upper test sites (right and left forearm) are moistened with warm water (90°–100° F.).
4. Product is dispensed, lather is generated and the timer is started.
5. The site is washed in a back and forth motion, one stroke per second. For 4-site arm wash a stroke is from the wrist to mid-arm and back to the wrist; or from the mid-arm to elbow and back to the mid-arm) for the designated time (e.g. 1 minute).
6. For washes over thirty seconds, technician's hands will be re-wet after half of the total time has elapsed and washing will continue.
7. The sites are rinsed with warm running water (90–100° F.) and patted dry.
8. The above procedure (1–7) is then repeated for the lower test sites For Bar Products: the bar is picked up, gloved hands and bar are moistened, and the bar is rotated ten times to generate the lather. A metronome may be used to guide the subjects washing rate.

Evaluation Methods

Same as the Standard Arm Wash.

Data Analysis

Same as the Standard Arm Wash.

Forearm Controlled Application Test (FCAT)

This controlled washing test is similar to that described by Ertel et al (*A forearm controlled application technique for estimating the relative mildness of personal cleansing products*, J. Soc. Cosmet. Chem., 46, 67 (1995)).

Subjects report to the testing facility for the conditioning phase of the study, which consists of using an assigned marketed personal washing cleanser for general use at home, up to four days prior to start of the product application phase. On Day 1 of the product application phase, a visual assessment is made to determine subject qualification. Subjects must have dryness scores ≦1.0 and erythema scores ≦0.5, and be free of cuts and abrasions on or near the test sites to be included in the product application phase. Subjects who qualify to enter the product application phase will then be instructed to discontinue the use of the conditioning product and any other skin care products on their inner forearms, with the exception of the skin cleansing test formulations that are applied during the wash sessions.

Qualified subjects will then have four 3.0-cm diameter (round) evaluation sites marked on each of the forearms using a skin safe pen (a total of eight sites). Visual evaluations for erythema and dryness will be conducted immediately prior to the first wash in each session and again in the afternoon of the final day (Day 5).

Washing Procedure for Bar Products:

1. Both arms are washed simultaneously. Test sites are treated in a sequential manner starting with the site closest to the flex area, ending with the site proximal to the wrist.
2. The sites closest to the flex area of the inner forearm of both the right and left arm are moistened with warm water (90°–100° F.).
3. A moistened Masslinn towel is rubbed in a circular motion on a wetted test bar for approximately 6 seconds by study personnel which will result in 0.2–0.5 g of product to be dispensed.
4. The site is washed with the designated product for 10 seconds followed by a 90-second lather retention phase.
5. The above procedure (1–4) is then repeated for each of the test sites. Sites are then be rinsed for fifteen seconds and patted dry.
6. Upon completion the entire procedure is repeated (two washes/session).

For Liquid Products: A technician will prepare liquid products just prior to the wash session by dispensing between 0.1 g and 0.5 g of product either directly onto the skin or a moistened Maslinn towel or alternative application material. The washing procedure outlined above will then be used.

Evaluation Methods

Baseline visual assessments are made prior to the start of the product application phase, and immediately before each wash session to evaluate dryness and erythema thereafter. The final visual evaluation is conducted on the afternoon of the final day. Washing of a test site will be discontinued if a clinical dryness or erythema score of >4.0 is reached, or at the subject's request. If only one arm is discontinued, the remaining arm will continue to be washed according to schedule. The same evaluator under conditions that are consistent throughout the study will conduct all of the visual evaluations. The 0–6 grading scale shown in Table 2 is used to assess the test sites for dryness and erythema. To maintain the evaluator's blindness to product assignment, visual assessments are conducted in a separate area away from the product application area.

TABLE 2

| Grade | Erythema | Dryness |
|---|---|---|
| 0 | None | None |
| 1.0 | Barely perceptible redness | Patches of slight powderiness and occasional patches of small scales may be seen. Distribution generalized |
| 2.0 | Slight redness | Generalized slight powderiness. Early cracking or occasional small lifting scales may be present. |
| 3.0 | Moderate redness | Generalized moderate powderiness and/or heavy cracking and lifting scales. |
| 4.0 | Heavy or substantial redness | Generalized heavy powderiness and/or heavy cracking and lifting scales |
| 5.0 | Extreme redness | Generalized high cracking and lifting scales. Powderiness may be present but not prominent. May see bleeding cracks. |
| 6.0 | Severe redness | Generalized severe cracking. Bleeding cracks. Bleeding cracks may be present. Scales large, may be beginning to disappear. |

Instrumental readings are taken on the first (baseline) and final day of the study.

A single Servo-Med Evaporimeter (TEWL) and three Skicon measurements will be taken on each test site, at baseline (prior to start of the first wash) and at the endpoint session (three hours after the last wash on Friday, or three hours after the wash where the subject receives a termination grade of 4 or greater). Subjects must equilibrate in the instrument room for a minimum of 30 minutes, exposing their arms. Subjects with baseline TEWL measurements of >10, which may be indicative of barrier damage, are not included in the product application phase of study.

Data Analysis

Within Test Product Effects

This protocol adopts as a working assumption the view promulgated by Ertel et al (Ertel, K. D., G. H. Keswick, and P. B. Bryant. *Forearm controlled application technique for estimating the relative mildness of personal cleansing products*., J. Soc. Cosmet. Chem., 46, 67 (1995)) that the dryness and erythema scales are linear. Hence, parametric statistical methods will be used. The effects of each test product will be examined by comparing the clinical grade at each time point versus the baseline clinical grade using a paired t-test. Statistical significance will be determined at the 90% confidence level (p-value 0.10) to determine if treatment results are statistically different from their baseline score and in which direction. (G. W. Snedecor and W. G. Cochran, Statistical Methods. Ames, Iowa. The Iowa State University Press, 1980, pp. 84–86).

Between Test Product Effects

For all treatments, differences will be statistically compared using an analysis of variance with panelist acting as a block to compare the extent of "change from baseline" among the treatments. Following the Ertel et al published model approach, the fixed effects analysis of variance is intended to account for varying skin conditions along the volar forearm surface as well as side (left arm versus right arm) differences.

The general model is: response ijklm=$\mu$+Ti+Sj+Ak+Pl+ljk+$\epsilon$ijklm where $\mu$=the grand mean T =effect due to treatment i S=effect due to treatment site j A=effect due to the side (arm), k, on which the treatment appears P=effect due to subject l I=a site * side interaction term $\epsilon$=an error term that includes error due to the various effects & experimental error, m.

with all effects other than error modeled as fixed effects.

If overall statistically significant differences are detected, pairwise treatment comparisons will be implemented by comparing the least square means using either Fisher's Least Significant Difference test (LSD) or Dunnett's test (if comparing treatments to a common control). The least square means are more accurate estimators than the regular means in that they adjust for other terms in the model and rectify slight imbalances which may sometimes occur due to missing data.

In addition, for each attribute, a survival analysis will examine treatment performance over wash sessions. The analysis will incorporate the number of wash sessions that a subject's treatment site is actually washed in the study. If the treatment site is discontinued, then the site's survival time is determined at that evaluation. An overlay plot of the estimated survival function for each treatment group will be examined. The Log-Rank test statistic will be computed to test for homogeneity of treatment groups. This test will tell if the survival functions are the same for each of the treatment groups.

2. Transepidermal Water Loss (TEWL)

The ServoMed Evaporimeter Model EP 1D, (ServoMed Inc, Broomall, Pa.) was used to quantify the rates of transepidermal water loss following the procedures similar to those outlined by Murahata et al ("*The use of transepidermal water loss to measure and predict the irritation response to surfactants*" Int. J. Cos. Science 8, 225 (1986)). TEWL provides a quantitative measure of the integrity of the stratum corneum barrier function and the relative effect of cleansers.

The operating principle of the instrument is based on Fick's law where $$(1/A)(dm/dt)=-D(dp/dx)$$

where

A=area of the surface ($m^2$)

m=weight of transported water (g)

t=time (hr)

D=constant, 0.0877 g-1h-1 (mm Hg)-1 related to the diffusion coefficient of water p=partial pressure of water vapor in air (mm Hg)

x=distance of the sensor from the skin surface (m)

The evaporation rate, dm/dt, is proportional to the partial pressure gradient, dp/dx. The evaporation rate can be determined by measuring the partial pressures at two points whose distance above the skin is different and known, and where these points are within a range of 15–20 mm above the skin surface.

The general clinical requirements are as follows:

1. All panelists are equilibrated for a minimum of fifteen minutes before measurements in a test room in which the temperature is controlled to 21+/−1° C. and 50+/−5% RH respectively.
2. The test sites are measured or marked in such a way that pre and post treatment measurements can be taken at approximately the same place on the skin.
3. The probe is applied in such a way that the sensors are perpendicular to the test site, using a minimum of pressure.

Probe Calibration is achieved with a calibration set (No. 2110) which is supplied with the instrument. The kit must be housed in a thermo-insulated box to ensure an even temperature distribution around the instrument probe and calibration flask.

The three salt solution used for calibration are LiCl, $[MgNO_3]_2$, and $K_2SO_4$. Pre-weighed amounts of slat at high purity are supplied with the kit instrument. The solution concentrations are such that the three solutions provide a RH of ~11.2%, ~54.2%, and ~97% respectively at 21° C.

General use of the instrument is as follows:

1. For normal studies, instrument readings are taken with the selector switch set for 1–100 g/m2h range
2. The protective cap is removed from the probe and the measuring head is placed so that the Teflon capsule is applied perpendicularly to the evaluation site ensuring that a minimum pressure is applied from the probe head. To minimize deviations of the zero point, the probe head should be held by the attached rubber-insulating stopper.
3. Subject equilibration time prior to prior to evaluation is 15 minutes in a temperature/humidity controlled room (21+/−1° C. and 50+/−5% RH respectively).
4. The probe is allowed to stabilize at the test site for a minimum of 30 seconds before data acquisition. When air drafts exist and barrier damage is high it is recommended to increase the stabilization time.
5. Data is acquired during the 15 seconds period following the stabilization time.

3. Hydration

The Corneometer Skin Hygrometer (Diastron Ltd., Hampshire, England) is a device widely used in the cosmetic industry. It allows high frequency, alternating voltage electrical measurements of skin capacitance to be safely made via an electrode applied to the skin surface. The parameters measured have been found to vary with skin hydration. However, they may also vary with many other factors such as skin temperature, sweat gland activity, and the composition of any applied product. The Corneometer can only give directional changes in the water content of the upper stratum corneum under favorable circumstances but even here the quantitative interpretations may prove misleading.

A widely used alternative is the Skicon Skin conductance Meter (I.B.S. Co Ltd. Shizuoka-ken, Japan).

Panelist Requirements for either instrument are as follows:

1. Subjects should equilibrate to room conditions, which are maintained at a fixed temperature and relative humidity (21+/−1° C. and 50+/−5% RH respectively) for a minimum of 15 minutes with their arms exposed. Air currents should be minimized.
2. Physical and psychological distractions should be minimized, e.g., talking and moving around.
3. Consumption during at least 1 hour before measurement of hot beverages or of any products containing caffeine should be avoided.
4. Panelists should avoid smoking for at least 30 minutes prior to measurements.

Operating procedure

1. The probe should be lightly applied so as to cause minimum depression of the skin surface by the outer casing. The measuring surface is spring-loaded and thus the probe must be applied with sufficient pressure that the black cylinder disappears completely inside the outer casing.
2. The probe should be held perpendicular to the skin surface.
3. The operator should avoid contacting hairs on the measure site with the probe.
4. The probe should remain in contact with the skin until the instrument's signal beeper sounds (about 1 second) and then be removed. Subsequent measurements can be made immediately provided the probe surface is known to be clean.
5. A minimum of 3 individual measurements should be taken at separate points on the test area and averaged to represent the mean hydration of the site.
6. A dry paper tissue should be used to clean the probe between readings.

4. Sensory Panel Evaluation

This evaluation protocol is used to differentiate the sensory properties of soap bars and employs a trained expert sensory panel. The methodology is a variant of that initially proposed Tragon and employs a language generation step.

The panel washes with each of up to a maximum of ten bars only once each, and will use the products up to a maximum of two per day. Each panelists washes their forearms using their normal habit for up to a maximum of 10 seconds, after which time they will rinse the product from their skin under running water. The panelists quantify various product attributes, using a line scale questionnaire, at various stages of the washing process. The key attributes evaluated include:

a) Bar feel b) Lather feel and appearance of hands during the initial lathering process c) Product/lather feel on the arm during washing d) Rinsability e) Wet skin feel after rinsing f) Dry skin feel after 2 minutes The water used was 40 PPM hardness expressed as PPM $CaCO_3$.

EXAMPLES

Example 1

The bar compositions shown in table 3 were prepared as follows. Cooled soap noodles, PAG, fatty acid, and protic acid (as acid or as the salt) were charged to a "Z blade" mixer and mixed for 30 minutes at a temperature of 30 C. The remaining ingredients were added and mixed an additional 30 minutes. The mass was then transferred to a three-roll mill, plodded into a billet, cut and finally stamped into bars.

TABLE 3

Bar compositions for Example 1

| Ingredient | Composition Weight % in Bar: Bar 1 (Comparative) | Bar 2 |
|---|---|---|
| Sodium soap 85% Tallow/15% Coconut Oil | 86 | 76.5 |
| Titanium Dioxide | 0.3 | 0.3 |
| EDTA | 0.06 | 0.06 |
| EHDP | 0.03 | 0.03 |
| White slurry* | 0.4 | 0.04 |
| Polyalkylene glycol Polyethylene glycol 600 (Mw = 600) | | 4.0 |
| Coconut Fatty Acid | — | 5.5 |
| Sodium Chloride (Protic acid salt) | 0.7 | 0.8 |
| Perfume | 0.7 | 0.7 |
| Water | 12.5 | 12.5 |

*White Slurry Composition

| | |
|---|---|
| Water | 97.32 |
| Sodium tripolyphosphate | 0.15 |
| Sodium Carbonate | 0.15 |
| Tinopol CBS (optical brightener) | 2.38 |

Bar 1 and Bar 2 were evaluated in the Arm Wash described above in the Methology Section.

The bars are compared in Table 4 and FIG. 1 for their ability to induce visual dryness as evaluated by an expert grader. It is clear that the inclusion of PAG in the soap bar composition significantly reduced the drying potential of the soap bar in this Controlled Wash Application Test.

The effects of PAG on the transepidermal water loss and hydration level of the skin are summarized in Table 5. The results demonstrate that the inclusion of the combination of polyethylene glycol 600 and fatty acid into the soap bar compositions reduces its potential to damage the skins barrier function (TEWL) and to lower the skins ability to hold water (increases hydration). The differences are highly significant.

TABLE 4

| Comparison Bar 1 and Bar 2 in Visual dryness as a Function of Time | | | | | | | |
|---|---|---|---|---|---|---|---|
| | Visual Dryness | | | | | | |
| | DAY 1 | DAY 2 | DAY 3 | DAY 4 | DAY 5 | CUMUL | LAST ASSESSMENT |
| Bar 2 | 1.26 | 2.06 | 2.67 | 3.39 | 5.06 | 13.65 | 1.66 |
| Bar 1 | 1.84 | 2.59 | 3.93 | 4.71 | 7.16 | 19.04 | 1.96 |
| Sig. Diff p = 0.05 | 0.36 | 0.51 | 0.49 | 0.63 | 0.84 | 1.42 | 0.17 |
| p Value | 0.0041 | 0.0429 | 0.0001 | 0.0004 | 0.0001 | 0.0001 | 0.0026 |

TABLE 5

| Instrumental assessment of Bar 1 and Bar 2 (contains PAG/FA) | | | | |
|---|---|---|---|---|
| | Transepidermal Water Loss (Evaporimeter gm/$M^2$/hr) | | Hydration estimated by Corneometer (a.u.) | |
| | Baseline | End Test | Baseline | End of test |
| Bar 1 | 2.80 | 16.04 | 73.8 | 44.9 |
| Bar 2 | 2.65 | 12.14 | 75.0 | 49.8 |
| Difference (Bar 2 − Bar 1) | −0.15 | −3.9 | 1.2 | +4.9 |
| P value | 0.33 | 0.03 | 0.2 | 0.008 |

As clearly noted, Bar 2 of invention has less water loss (leading to moisturized feeling skin) than Comparative Bar 1 which does not have PEG or PEG in combination with protic acid salt.

Example 2

This example illustrates the reduction in visual dryness, and barrier damage, and the improvement in skin hydration accompanying the introduction of PAG into soap bars having two different soap compositions. The Bar compositions 3–6 shown in Table 6 were prepared by the procedures described in Example 1.

TABLE 6

| Bar composition prepared for Example 2. | | | | |
|---|---|---|---|---|
| | Composition Weight % in Bar | | | |
| Ingredient | Bar 3 (Comparative) | Bar 4 | Bar 5 (Comparative) | Bar 6 |
| Sodium soap 85% Tallow/ 15% Coconut Oil | 85.0 | 71.5 | | |
| Sodium soap 65% Palm Stearin/ 35% Coconut Oil | | | 85.0 | 71.5 |
| Titanium Dioxide | 0.3 | 0.3 | 0.3 | 0.3 |
| EDTA | 0.02 | 0.02 | 0.02 | 0.02 |
| EHDP | 0.02 | 0.02 | 0.02 | 0.02 |
| Polyalkylene glycol Polyethylene glycol 600 (Mw = 600) | | 5.0 | | 5.0 |
| Fatty Acid Blend (C12, C14, C16, C18) | | 6.5 | | 6.5 |
| Sodium Citrate | | 2.1 | | 2.1 |
| Perfume | 1.0 | 1.0 | 1.0 | 1.0 |
| Water | 12.0 | 12.0 | 12.0 | 12.0 |

These bar compositions were evaluated by the 4-site arm wash protocol described in the Methodology Section. The results are summarized in Table 7A and 7B. It is clear that the inclusion of PAG in either of the soap bar composition significantly reduced the drying potential of these soap bars: Compare Bar 4 with Bar 3 (Table 7A) and Bar 6 with Bar 5 (Table 7B). The results are shown graphically in FIGS. 2 and 3.

The effects of PAG/FA/protic acid salt on the transepidermal water loss and hydration level of the skin are summarized are also summarized in Table 7. The results demonstrate that the inclusion of the combination of polyethylene glycol 600 and fatty acid into the soap bar compositions reduces its potential to damage the skins barrier function (TEWL) and to increase the skins ability to hold water (increases hydration).

TABLE 7A

| 4 sight arm wash results Bar 4 Vs Bar 3 | | | |
|---|---|---|---|
| Product | Dryness Change from Baseline | TEWL | Skicon |
| Bar 3 | 0.78 | 4.14 | −126.53 |
| Bar 4 | 0.64 | 3.55 | −89.09 |
| Conclusion | Significant | Significant | Significant |
| p-value | 0.0033 | 0.0583 | 0.0171 |

TABLE 7B

| 4 sight arm wash results Bar 6 Vs Bar 5 | | | |
|---|---|---|---|
| Product | Dryness Change from Baseline | TEWL | Skicon |
| Bar 5 | 0.78 | 3.53 | −144.8 |
| Bar 6 | 0.64 | 3.55 | −118.96 |

TABLE 7B-continued 4 sight arm wash results Bar 6 Vs Bar 5

| Product | Dryness Change from Baseline | TEWL | Skicon |
|---|---|---|---|
| Conclusion | Significant | Not Significant | Significant |
| p-value | 0.0042 | 0.500 | 0.0616 |

Example 3

This example further illustrates the influence of PAG in improving the skin condition performance of soap bar. The bar compositions shown in Table 8 were prepared. These bars were evaluated for their ability to induce dryness utilizing the FCAT protocol described in the Methodology Section.

TABLE 8

Bar composition prepared for Example 3.

| Ingredient | Composition Weight % in Bar Bar 7 (Comparative) | Bar 8 (Comparative) | Bar 9 | Bar 10 |
|---|---|---|---|---|
| Sodium soap 85% Tallow/15% Coconut Oil | 85.0 | 55 | 55 | 55 |
| Talc | | 32 | 12 | 15 |
| Titanium Dioxide | 0.3 | | | |
| EDTA | 0.02 | | | |
| EHDP | 0.02 | | | |
| Polyalkylene glycol | | | 12 | 9 |
| Polyethylene glycol 8000 (Mw = 8000) | | | | |
| Coco amidopropyl betaine | | | | 2 |
| Fatty Acid Blend (C12, C14) | | | 8 | 6 |
| Sodium Citrate | | | | |
| Perfume | 1.0 | | | |
| Water | 14 | 12 | 12 | 12 |

The results of instrumental assessments at the end-point are shown in Table 9. The inclusion of PAG in Bar 9 and Bar 10 significantly reduces ($P<0.05$) damage to the barrier function of the skin as demonstrated by lower rate transepidermal water loss following treatment than with Bar 7 or Bar 8. It is also clear from the Skicon measurements that skin washed with either Bar 9 or Bar 10 which both contain PAG and fatty acid retain a higher level of water following than skin washed with the ordinary soap compositions (Bar 7 and Bar 8).

TABLE 9

Instrumental results at end-point following the FCAT protocol: Bars 7–10

| | Bar 7 | Bar 8 | Bar 9 | Bar 10 |
|---|---|---|---|---|
| TEWL Change from Baseline (Evaporimeter gm/$M^2$/hr) | 2.85 | 3.28 | 1.54 | 2.03 |
| Hydration estimated from Skicon (arbitrary units) | −98.9 | −87.4 | −54.5 | −44.8 |

Thus in three different wash protocol, the benefits of PAG in combination with fatty acid are evident.

Example 4

This example illustrates that bar compositions containing the PAG, organic protic acid salt, and fatty acid defined herein provide improved skin care without reducing the clean and refreshing experience of washing with soap that is preferred by many consumers.

The bar compositions identified in Table 10 were prepared by the procedure that are described in Example 1.

TABLE 10

Bar compositions used in consumer testing for Example 4

| Composition (%) | Bar 11 | Bar 12 | Bar 13 | Bar 14 | Bar 15 |
|---|---|---|---|---|---|
| Sodium soap Tallow/ Coconut Oil ratio | 85/15 | 85/15 | 10/90 | 85/15 | 85/15 |
| Anhydrous Sodium soap | 74.19 | 82.77 | 71.11 | 72.32 | 74.30 |
| Sodium Citrate | 2.0 | | 2.0 | | |
| Titanium Dioxide | 0.4 | 0.4 | 0.4 | 0.4 | 0.4 |
| EDTA | 0.04 | 0.04 | 0.04 | 0.03 | 0.04 |
| EHDP | 0.02 | 0.02 | 0.02 | 0.02 | 0.02 |
| Poly ethylene glycol 600 (Mw = 600) | 4.00 | | | | |
| Paraffin Wax | | | | | 10.0 |
| Glycerol | | | 9.30 | 6.13 | |
| Fatty Acid Blend C12–C18 | 5.5 | | 5.25 | | |
| Coconut Fatty Acid (added) | | | | 0.50 | |
| Perfume | 1.50 | 1.50 | 1.50 | 1.50 | 1.50 |
| Water | 13.00 | 13.50 | 10.00 | 17.50 | 12.5 |
| Minors Ingredient up to | 100 | 100 | 100 | 100 | 100 |

Bars 11–15 were evaluated in two consumer panels. One panel comprised self-perceived oily skin consumers while the other comprised self perceived dry skin (200 consumers in each group). Bar 11 and 12 were preferred on lather and rinsing properties among oily skin consumers. Bar 11 was preferred to ordinary soap (Bar 12) and also to Bar 13–15 overall by consumers who had self perceived dry skin for leaving the skin more moisturized.

Thus the method of cleansing with a soap bar incorporating PAG and fatty acid in the desired ratios is preferred by oily skin consumers for its cleansing properties. Simultaneously, this method is also preferred by dry skin consumers for its better skin care properties.

Example 5

This example illustrates the criticality in selecting the proper ratios of fatty acid, polyalkylene glycol, and protic acid salts to achieving bars that can be manufactured economically and have good in-use properties. A series of soap bars compositions were prepared that incorporated different levels of fatty acid, PAG and protic acid salt in various ratios. All bars contained either a blend of 85/15 or 80/20 non-lauric (e.g., from tallow) to lauric (e.g., from coconut oil) soaps. The moisture content ranged from 10% to 16% with a center point at 13%, which considered the standard.

In this example the PAG was polyethylene glycol having a molecular weight of 600, the protic acid salt was sodium citrate, and the fatty acid was a blend comprising C12 to C18 chain length soaps. The bars fell into three classes depending on the weight ratio of Fatty acid to (PAG+protic acid salt). When this ratio was too low the bars lacked sufficient cohesion and tended to crumble easily: "crumbly". When the ratio was too high, the bars were too sticky to be properly extruded and stamped at the process temperature: "sticky". In between these limits the compositions were processible, and had good bar and in-use properties, e.g., did not crack, lathered well, etc.

The critical limits on the FA/(PAG+Protic Acid Salt) ratios for these moisture contents are show in FIG. 4. The critical FA/PAG range varies somewhat with water content but is about 0.5 to about 2.0, i.e., in a ratio of 1:2 to 2:1.

Example 7

Bar compositions relevant to the instant invention are illustrated in Table 11.

TABLE 11

Examples of relevant bar compositions

| Ingredient | Composition Weight % in Bar | | | | | |
|---|---|---|---|---|---|---|
| | Bar 16 | Bar 17 | Bar 18 | Bar 19 | Bar 20 | Bar 21 |
| Sodium soap 85% Tallow/15% Coconut Oil | 70 | 65.0 | 64.2 | | | |
| Sodium soap 65% Palm Stearin/35% Coconut Oil | | | | 75.6 | 68.6 | 65.0 |
| Titanium Dioxide | 0.3 | 0.3 | 0.3 | 0.3 | 0.3 | 0.3 |
| EDTA | 0.02 | 0.02 | 0.02 | 0.02 | 0.02 | 0.02 |
| EHDP | 0.02 | 0.02 | 0.02 | 0.02 | 0.02 | 0.02 |
| Polyalkylene glycol Polyethylene glycol 600 (Mw = 600) | 4 | 2 | 5 | 4 | 3 | 6 |
| Sunflower seed oil | 4 | 2 | 2 | 2 | 3 | |
| Vitamin C acetate | .2 | | | 0.1 | | 0.2 |
| Calcium Carbonate | | 5 | | | | 4 |
| Talc | | | 4 | | 4 | |
| Coco amidopropyl betaine | | | | | | 2 |
| Fatty Acid Blend (C12, C14) | 5.5 | | | | 5 | |
| Fatty acid Blend (C10–C18) | | 4 | 6 | 5.5 | | 6 |
| Sodium cocoyl isethionate | | | 2 | | | 1 |
| Petrolatum | | 2 | 2 | | 2 | 2 |
| Silicone oil (60,000 cst) | 2 | 2 | | | 1 | 1 |
| Sodium Citrate (organic protic acid salt) | 0.9 | 1.5 | 2.5 | 2.0 | | 1.5 |
| Sodium Chloride (inorganic protic acid salt) | | | | | 0.8 | 1.5 |
| Perfume | 1.0 | 1.0 | 1.0 | 1.0 | 1.0 | 1.0 |
| Water | 13 | 12 | 11 | 10 | 13 | 10 |

Example 8

Bar compositions relevant to the instant invention are further illustrated in Table 12.

TABLE 12

Examples of relevant bar compositions

| Ingredient | Composition Weight % in Bar | | | | | | | | |
|---|---|---|---|---|---|---|---|---|---|
| | Bar 22 | Bar 23 | Bar 24 | Bar 25 | Bar 26 | Bar 27 | Bar 28 | Bar 29 | Bar 30 |
| Sodium soap 85% Tallow/15% Coconut Oil | 73.4 | 60.2 | 71.7 | | 71.5 | | 79.5 | | 60.6 |
| Sodium soap 65% Palm Stearin/35% Coconut Oil | | | | 75.2 | | 70 | | 74 | |
| Titanium Dioxide | 0.3 | 0.3 | 0.3 | 0.3 | 0.3 | 0.3 | 0.3 | 0.3 | 0.3 |
| EDTA | 0.02 | 0.02 | 0.02 | 0.02 | 0.02 | 0.02 | 0.02 | 0.02 | 0.02 |
| EHDP | 0.02 | 0.02 | 0.02 | 0.02 | 0.02 | 0.02 | 0.02 | 0.02 | 0.02 |
| Polyalkylene glycol Polyethylene glycol 10,000 (Mw = 10000) | | 8 | | | 4 | | | | 10 |
| Polyalkylene glycol Polyethylene glycol 600 (Mw = 600) | 4 | | 5 | 4 | | 6 | 4.5 | 5 | |
| Sunflower seed oil | | 2 | | | | | | 2 | 2 |
| Vitamin E | 0.2 | | 0.1 | 0.1 | | 0.2 | | 0.1 | |
| Niacinamide | | | | | | | 1.0 | | |
| Sea weed extract | | | 0.5 | 0.5 | | | | | |
| Triclocarban (antimicrobial) | | | | | 1.4 | | | | |
| Irgasan DP 300 (antimicrobial) | | | 0.3 | 0.25 | 0.25 | | | | |
| Vitamin C | 0.1 | | 0.1 | 0.1 | | | | 0.1 | |
| Parcol MCX (Sunscreen) | | | | | | | | | 1 |
| Sodium Citrate (tribasic) | | 2.5 | 2.5 | 2 | | | | | 3 |
| Sodium Lactate | | | | | | | 2.7 | 2.5 | |
| Sodium adipate | 2.5 | | | | 2.5 | | | | |
| Jaguar 13 S (Cationic polymer) | | 1 | | | | 2.5 | | | 1 |
| Fatty acid Blend (C10–C18) | 5.5 | 6 | 5.5 | 5.5 | 5.5 | 7 | | | 8 |

TABLE 12-continued

Examples of relevant bar compositions

| Ingredient | Composition Weight % in Bar | | | | | | | | |
|---|---|---|---|---|---|---|---|---|---|
| | Bar 22 | Bar 23 | Bar 24 | Bar 25 | Bar 26 | Bar 27 | Bar 28 | Bar 29 | Bar 30 |
| Sodium cocoyl isethionate | | 2 | | | | | | | |
| Petrolatum | | 2 | | | | | | 2 | 1.6 |
| Silicone oil (60,000 cst) | | 1 | | | | | 1 | | 1.5 |
| Perfume | 1.0 | 1.0 | 1.0 | 1 | 1.5 | 1 | 1.0 | 1.0 | 1.0 |
| Water | 13 | 12 | 13 | 11 | 13 | 13 | 10 | 13 | 11 |

Example 9

This example further illustrates the influence of PAG/FA/Protic acid salt in improving the skin condition performance of soap bar. The bar compositions shown in Table 14 were prepared. These bars were evaluated for their ability to induce dryness utilizing the FCAT protocol described in the Methodology Section.

TABLE 13

Bar composition prepared for Example 9

| Ingredient | Composition Weight % in Bar | |
|---|---|---|
| | Bar 31 | Bar 32 |
| Sodium soap | 86.5 | 71.3 |
| 85% Tallow/15% Coconut Oil | | |
| Dimethicone | | 1.0 |
| Free fatty acid | | 4.0 |
| EDTA | | 0.02 |
| EHDP | | 0.04 |
| Polyalkylene glycol | | |
| Polyethylene glycol 600 (Mw = 600) | | 4.0 |
| Titanium dioxide | | 0.4 |
| Fatty Acid Blend (C12, C14) | | |
| Sodium Chloride | | |
| Sodium Citrate | 0.5 | 1.5 |
| Tinopal CBS | | 0.024 |
| Perfume | | 1.27 |
| Glycerin, sodium chloride | | <1.5 |
| Water | 13.0 | 14.0 |

The results of Skicom instrumental assessments at the end-point are shown in Table 15. It is also clear from the Skicon measurements that skin washed with Bar 32 that contained 4% PAG retains a higher level of water than skin washed with the ordinary soap compositions, Bar 31.

TABLE 14

Instrumental results at end-point following the FCAT protocol:

| Change in Skicom from Baseline | Bar 31 | Bar 32 |
|---|---|---|
| Hydration estimated from Skicon (arbitrary units) | −18.24 | −36.36 |

As clearly seen, bar 32 is superior to bar 31 (i.e., has higher conductivity).

What is claimed is:

1. A bar composition comprising:

(a) 25 to 85% by weight fatty acid soap;

(b) polyalkylene glycol having MW of 400 to 25,000 Dalton;

(c) $C_8$ to $C_{20}$ free fatty acid;

(d) 0.1 to 5% by wt. of a salt of protic acid having pKa1 less than 6;

wherein the amount of polyalkylene glycol (b) present in the bar is sufficient to improve skin condition in controlled application wash tests either by reducing the barrier damage as measured by transepidermal water loss, increasing skin hydration as measured by skin conductivity/capacitance, and/or by reducing visual dryness;

wherein, the molar equivalents ratio of free fatty acid (c) to protic acid salt (d) is between 0.5:1 to 3:1, and the weight ratio of free fatty acid (c) to the sum of weights of polyalkylene glycol plus organic protic acid salt ((b) and (d)) is 1:2 to 2:1.

2. A composition according to claim 1, wherein the polyalkylene glycol is a polyethylene glycol having a MW of 400 to 10,000 and is present in the composition at a level of from 1.5 to 25% by wt.

3. A composition according to claim 1, wherein free fatty acid is a saturated or unsaturated fatty acid having from 8 to 20 carbon atoms and is present at a level of from 0.1% to 14% by wt.

4. A composition according to claim 1 comprising 0.5 to 3% by wt. salt of protic acid.

5. A composition according to claim 1, wherein protic acid salt has pKa1 less than 5.5.

6. A composition according to claim 1 wherein said protic acid salt is an organic protic acid salt and is selected from the group consisting of the magnesium, potassium and sodium salts of adipic acid, citric acid, glycolic acid, formic acid, fumaric acid, lactic acid, malic acid , maleic acid, succinic acid, tartaric acid, salicylic acid and their mixtures thereof.

7. A composition according to claim 1 wherein said protic acid salt is an inorganic protic acid salt and is selected from the group comprising the magnesium, potassium and sodium salts of hydrochloric acid, sulfuric acid, phosphoric acid and mixtures thereof.

8. A composition according to claim 1 wherein said protic acid is selected from the group consisting of the sodium salts or potassium salts of hydrochloric acid, adipic acid, citric acid, and lactic acid and mixtures thereof.

9. A composition according to claim 1, wherein molar equivalent ratio of fatty acid to salt of protic acid is 0.75:1 to 2:1.

10. A composition according to claim 1, wherein the wt. ratio of free fatty acid to polyalkylene glycol plus salt of protic acid is 1:1.5 to 1.5:1.

11. A method of claim 1 where the bar composition also contains from 0.5–10 wt % of an auxiliary surfactant selected from the group consisting of acyl isethionates, alcohol ethoxylates, fatty acid esters of polyethylene glycol, alkene sulfonates, alkyl betaines, and alkyl amido propyl betaines.

12. A bar composition used for cleansing the skin comprising (a) 65–80 wt. % fatty acid soap consisting of a blend of fatty acid soaps derived from non-lauric fats/oils and lauric fats/oils blended in a ratio of from 95/5 to 50/50.

(b) 2–8 wt. % of a polyalkylene glycol of molecular weight 400–8000.

(c) 3–8 wt. % of C12–C18 fatty acids (d) 0.5–3 wt. % of an protic acid salt selected from the group consisting of sodium chloride, sodium citrate, sodium adipate, sodium lactate, sodium glycolate, and mixtures.

13. A bar composition of claim 12 which also contains from 0.1 to 10 wt. % of moisturizing benefit agents selected from the group consisting of: sunflower seed oil soy, bean oil, borage seed oil, primrose oil, essential fatty acids, petrolatum, mineral oil, vitamin A, C, and E, glycerol, salts of lactic acid and pyrollidone carboxylic acid, amino acids, proteins, and mixtures thereof.

14. A bar composition of claim 12 wherein the bar composition also contains from 0.1 to 10 wt. % of benefit agent useful for the treatment of oily skin selected from the group consisting of minerals, clays, plant extracts, sea/algae extracts, vitamins, inorganic salts, silica, talc, alpha and beta hydroxyacid salts and mixtures thereof.

15. A bar composition of claim 12 which additionally contains from 0.1 to 10 wt. % of skin renewal benefit agent selected from the group consisting of ceramides and pseudoceramides, niacinamide, vitamin C and its derivatives and mixtures thereof.

16. A bar composition of claim 12 which additionally contains from 0.1 to 5 wt. % of an antimicrobial agent.

17. A method for cleansing the skin that provides effective cleansing and improved skin care relative to using ordinary soap comprising washing the skin with an effective amount of water and a bar comprising:

(a) 25 to 85% by weight fatty acid soap;

(b) polyalkylene glycol having MW of 400 to 25,000 Dalton;

(c) $C_8$ to $C_{20}$ free fatty acid;

(d) 0.1 to 5% by wt. of a salt of protic acid having pKa1 less than 6;

wherein the amount of polyalkylene glycol (b) present in the bar is sufficient to improve skin condition in controlled application wash tests either by reducing the barrier damage as measured by transepidermal water loss, increasing skin hydration as measured by skin conductivity/capacitance, and/or by reducing visual dryness;

wherein, the molar equivalents ratio of free fatty acid (c) to protic acid salt (d) is between 0.5:1 to 3:1, and the weight ratio of free fatty acid to the sum of weights of polyalkylene glycol plus organic protic acid salt ((b) and (d)) is between 1:2 to 2:1.

18. A method for cleansing the skin that provides effective cleansing and improved skin care relative to using ordinary soap comprising washing the skin with an effective amount of water and a bar comprising:

(a) 65–80 wt. % fatty acid soap consisting of a blend of fatty acid soaps derived from non-lauric fats/oils and lauric fats/oils blended in a ratio of from 95/5 to 50/50.

(b) 2–8 wt. % of a polyalkylene glycol of molecular weight 400–8000.

(c) 3–8 wt. % of C12–C18 fatty acids.

(d) 0.5–3 wt. % of an protic acid salt selected from the group consisting of sodium chloride, sodium citrate, sodium adipate, sodium lactate, sodium glycolate, and their mixtures.

19. A method of claim 18 which also contains from 0.1 to 10 wt. % of moisturizing benefit agents selected from the group consisting of: sunflower seed oil, soy bean oil, borage seed oil, primrose oil, essential fatty acids, petrolatum, mineral oil, vitamin E, glycerol, salts of lactic acid and pyrollidone carboxylic acid, amino acids, proteins and mixtures thereof.

20. A method of claim 18 wherein the bar composition also contains from 0.1 to 10 wt. % of benefit agent useful for the treatment of oily skin selected from the group consisting of minerals, vitamins, clays, plant extracts, sea/algae extracts, silica, alpha and beta hydroxyacids, inorganic silica, talc, alhpa and beta hydroxy acid salts, and mixtures thereof.

21. A method of claim 18 which additionally contains from 0.1 to 10 wt. % of skin renewal benefit agent selected from the group consisting of: alpha and beta hydroxy acids and their salts including lactic acid, glycolic acid salicylic acid, ceramides and pseudoceramides, niacinamide, vitamin C and its derivatives and their combination.

22. A method composition of claim 18 which additionally contains from 0.1 to 5 wt. % of an antimicrobial agent.

* * * * *